(12) United States Patent
Avevor

(10) Patent No.: US 9,144,668 B1
(45) Date of Patent: Sep. 29, 2015

(54) EXPANDABLE DEVICE FOR INDEPENDENTLY INFLATING, DEFLATING, SUPPLYING CONTRAST MEDIA TO AND MONITORING UP TO TWO BALLOON CATHETERS FOR ANGIOPLASTY

(71) Applicant: Philip Avevor, Jacksonville, FL (US)

(72) Inventor: Philip Avevor, Jacksonville, FL (US)

( * ) Notice: Subject to any disclaimer, the term of this patent is extended or adjusted under 35 U.S.C. 154(b) by 9 days.

(21) Appl. No.: 14/224,094

(22) Filed: Mar. 25, 2014

(51) Int. Cl.
*A61M 29/00* (2006.01)
*A61M 25/10* (2013.01)

(52) U.S. Cl.
CPC ....... *A61M 25/10181* (2013.11); *A61M 25/104* (2013.01); *A61M 25/10185* (2013.11); *A61M 25/10187* (2013.11); *A61M 2205/3331* (2013.01)

(58) Field of Classification Search
CPC ..................... A61M 25/10181; A61M 25/104; A61M 25/10185; A61M 25/10187; A61M 2205/3331
USPC ................................. 604/98.01, 99.01, 99.02
See application file for complete search history.

*Primary Examiner* — Kevin C Sirmons
*Assistant Examiner* — Deanna K Hall
(74) *Attorney, Agent, or Firm* — Mark Young, PA

(57) ABSTRACT

An expandable inflation device for up to two balloon catheters for angioplasty includes a plurality of three port valves controlling flow to two fluid channels each coupled at an outlet to a balloon catheter for angioplasty. In line pressure gauges, which may be removable, monitor pressure of each channel. Each balloon catheter may be inflated and deflated, sequentially inflated, simultaneously inflated, sequentially deflated, simultaneously deflated, inflated to the same pressures, inflated to different pressures, partially deflated, and fully deflated.

20 Claims, 16 Drawing Sheets

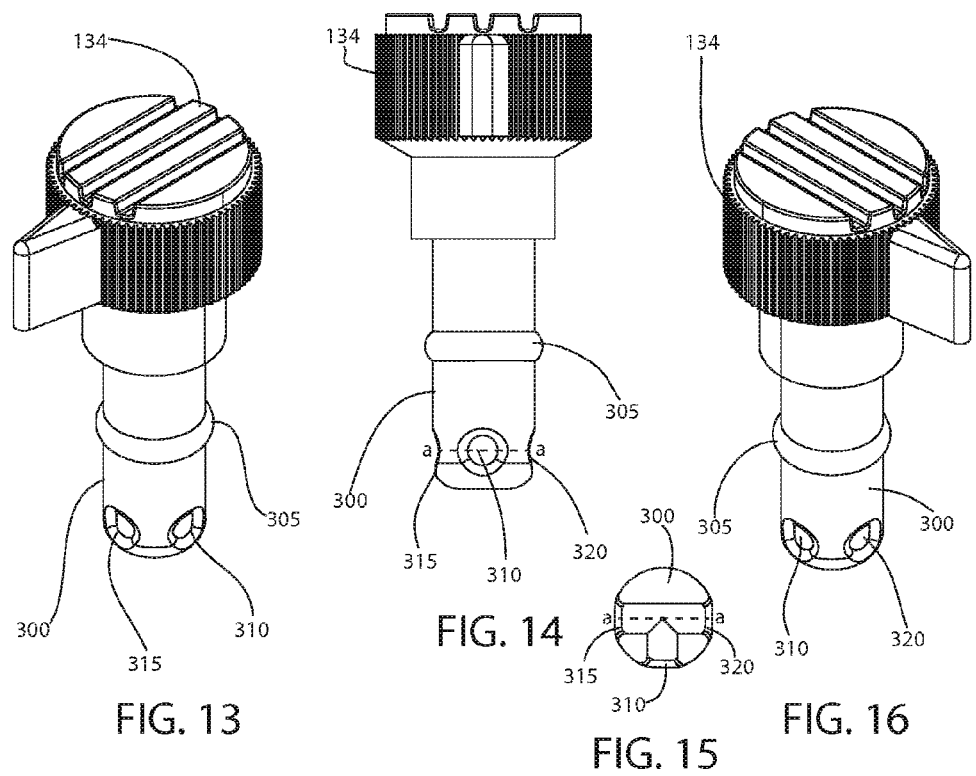

US 9,144,668 B1

EXPANDABLE DEVICE FOR INDEPENDENTLY INFLATING, DEFLATING, SUPPLYING CONTRAST MEDIA TO AND MONITORING UP TO TWO BALLOON CATHETERS FOR ANGIOPLASTY

FIELD OF THE INVENTION

This invention relates to angioplasty, and, more particularly, to an expandable fluid dispensing and inflation device for balloon angioplasty for independently inflating and deflating up to two separate balloons using a single plunger and independently supplying radiopaque contrast medium through up to two catheters.

BACKGROUND

Angioplasty entails mechanically widening narrowed or obstructed arteries, such as arteries obstructed from atherosclerosis. An empty and collapsed balloon on a guide wire, known as a balloon catheter, is fed into a vessel to the narrowed location and then inflated to a fixed size using fluid (e.g. water) pressure of about 5 to 30 atmospheres. Typically, a balloon is inflated with sufficient pressure (4-12 atm) to fully expand the stenosis indentation (dumbbell or waist) of the partially inflated balloon. Occasionally, some calcified or highly fibrotic lesions require very high inflation pressures (>14 atm) to expand and eliminate the "dumbbell" appearance of the balloon. Overinflation of the balloon increases the risk of artery dissection. The inflated balloon forces open the obstruction comprised of white blood cell/clot and plaque deposits and expands surrounding muscular wall of the vessel, opening up the blood vessel for improved flow. The balloon is then deflated and withdrawn. A stent may or may not be inserted at the time of ballooning to ensure the vessel remains open.

A bifurcation lesion involves a clinically relevant side branch. Plaque may be located either in both branches or in the main vessel only or in the side branch only. The carina is the flow divider that lies between the main branch and side branch and is the region of high flow and high shear stress.

One angioplasty technique for plaque at a bifurcation is the "kissing balloon" technique. Noncompliant balloons, each having a balloon size that is about same size as the vessel (usually a slightly smaller diameter balloon for the side branch) are used. A balloon is first fed into the side branch so that it protrudes into the side branch and extends into the main branch, but not proximal to a stent. The balloon may be fed into a stent in the side branch. Another balloon (shorter than the main branch stent) is advanced to the main branch so it lies within the main branch but not extending beyond the confines of the stent in the main branch. The balloons are inflated simultaneously. Then the balloons are deflated simultaneously to avoid distortion. In a variation of the basic technique, the side branch balloon is inflated to high pressure (>20 atm, perhaps 24 or 26 atm) and then deflated. Then the main branch balloon is inflated to moderate pressure and deflated. Then, both balloons are simultaneously inflated at low pressure to correct any distortion caused by sequential balloon inflation. These procedures require the ability to independently inflate, maintain inflated, monitor pressure in, and deflate each balloon.

Unfortunately, devices available today do not provide the ability to independently inflate, maintain inflated, monitor pressure in, and deflate each balloon in a kissing balloon procedure. Instead, many practitioners use two separate indeflator devices to inflate, monitor and deflate each balloon independently. While effective, such an approach is not without problems. Managing two separate, but abutting, indeflators in limited available space, with several tubes extending to and from each indeflator, presents challenges to the practitioner and great risk of confusing one indeflator for the other.

Often it is not known if a second catheter is required for a procedure until the procedure is underway. A means for adding a "kissing balloon" module while a procedure is underway is needed.

Thus, what is needed is a device that facilitates independently supplying radiopaque contrast medium through one or more catheters, while independently inflating, monitoring and deflating up to two distal balloons using an expandable device, to which a second module can be added if and when needed.

SUMMARY OF THE INVENTION

An expandable inflation device for up to two balloon catheters for angioplasty is provided. The two balloon catheters include a first catheter and a second catheter. In an exemplary implementation, the inflation device includes a pump mechanism having a tubular reservoir with an outlet and a longitudinal axis, and piston movable linearly through the tubular reservoir along the longitudinal axis, and a manually operated actuator coupled to the piston and controlling linear motion of the piston. A primary three-port valve has a first primary port in fluid communication with the outlet of the pump, a second primary port and a third primary port. The primary three port valve is switchable between a first state in which the first primary port, second primary port and third primary port are in fluid communication, and a second state in which the first primary port and second primary port are in fluid communication, and a third state in which the first primary port and third primary port are in fluid communication, and a fourth state in which the second primary port and third primary port are in fluid communication. A first pressure measuring device is in fluid communication with the second primary port of the primary three-port valve. A second pressure measuring device is mechanically and fluidly attachable. When attached, the second pressure measuring device is in fluid communication with the third primary port of the primary three-port valve. A first outlet port is in fluid communication with the first pressure measuring device and the second primary port of the primary three-port valve. The first outlet port is attachable to the first catheter. A second outlet port is in fluid communication with the second pressure measuring device and the third primary port of the primary three-port valve. The second outlet port is attachable to the second catheter.

The inflation device may further include a left intermediate three-port valve disposed and fluidly coupled between the second primary port of the primary three-port valve and the first pressure measuring device. Such a left intermediate three-port valve may have a first left intermediate port, a second left intermediate port and a third left intermediate port. The left intermediate three port valve is switchable between a first state in which the first left intermediate port, second left intermediate port and third left intermediate port are in fluid communication, and a second state in which the first left intermediate port and second left intermediate port are in fluid communication, and a third state in which the first left intermediate port and third left intermediate port are in fluid communication, and a fourth state in which the second left intermediate port and third left intermediate port are in fluid communication. The first left intermediate port is fluidly coupled to the second primary port of the primary three-port valve. The third left intermediate port is fluidly coupled to the first pressure measuring device. The second left intermediate port is available for accessory attachment.

The inflation device may further include a right intermediate three-port valve disposed and fluidly coupled between the third primary port of the primary three-port valve and the second pressure measuring device. Such a right intermediate three-port valve may have a first right intermediate port, a second right intermediate port and a third right intermediate port. The right intermediate three port valve is switchable between a first state in which the first right intermediate port, second right intermediate port and third right intermediate port are in fluid communication, and a second state in which the first right intermediate port and second right intermediate port are in fluid communication, and a third state in which the first right intermediate port and third right intermediate port are in fluid communication, and a fourth state in which the second right intermediate port and third right intermediate port are in fluid communication. The first right intermediate port is fluidly coupled to the third primary port of the primary three-port valve. The third right intermediate port is fluidly coupled to the second pressure measuring device. The second right intermediate port is available for accessory attachment.

The second right intermediate port includes a threaded fluid fitting, such as a Luer-Lock. Likewise, the second left intermediate port may include a threaded fluid fitting, such as a Luer-Lock. Similarly, each of the first and second outlet ports may comprise threaded fittings, such as Luer-Lock fittings.

The manually operated actuator coupled to the piston of the pump mechanism may be a threaded shaft having one end coupled to the piston and a proximal end opposite the end coupled to the piston. A graspable rotatable handle, such as a knob, may be attached to the proximal end of the threaded shaft.

Each of the first and second pressure measuring devices may be threadedly engaged and removable. Each of the first and second pressure measuring devices may measure pressure up to and less than 30 atm.

The second pressure measuring device may be contained in a secondary module that may be attached if and when needed for treating a bifurcation. Thus, a physician may commence a procedure with a primary module. If the secondary module is needed, it may be readily attached during the procedure. In this way, the added cost and complexity of the secondary module is avoided unless it is needed.

When the secondary module is added, each balloon catheter may be inflated and deflated, sequentially inflated, simultaneously inflated, sequentially deflated, simultaneously deflated, inflated to the same pressures, inflated to different pressures, partially deflated, and fully deflated. Pressure in each balloon catheter may be monitored. Through accessory ports 137, 142 fluids (e.g., saline or contrast media) may be introduced into or evacuated from a balloon catheter. Additionally, to evacuate a catheter before filling with a fluid such as saline and contrast media, a suction device may connected to each accessory port 137, 142 while a catheter is attached to each outlet 175, 180. The suction device may comprise a syringe or other device capable of substantially evacuating a balloon catheter. Pressure gauges may be fixed and may be identical or different. Alternatively, pressure gauges may be removable and the same or different. Pressure gauges may be removed and replaced. Fluids (e.g., saline or contrast media) may be introduced or added to the pump and branches, even during a procedure, without deflating a catheter. An indeflator according to principles of the invention thus provides enhanced versatility over conventional indeflators, which do not facilitate simultaneous inflation or deflation, and do not allow removal of pressure gauges, and do not allow inflation and deflation of both balloon catheters through a single pump.

BRIEF DESCRIPTION OF THE DRAWINGS

FIG. 13 provides a perspective view of an exemplary three-way valve for balloon angioplasty with two balloon catheters according to principles of the invention; and FIG. 14 provides a front view of an exemplary three-way valve for balloon angioplasty with two balloon catheters according to principles of the invention; and FIG. 15 provides a section view (a-a) of a portion of an exemplary three-way valve for balloon angioplasty with two balloon catheters according to principles of the invention; and FIG. 16 provides a perspective view of an exemplary three-way valve for balloon angioplasty with two balloon catheters according to principles of the invention.

Those skilled in the art will appreciate that the figures are not intended to be drawn to any particular scale; nor are the figures intended to illustrate every embodiment of the invention. The invention is not limited to the exemplary embodiments depicted in the figures or the specific components, steps, configurations, shapes, relative sizes, ornamental aspects or proportions as shown in the figures.

DETAILED DESCRIPTION

Figure 1:
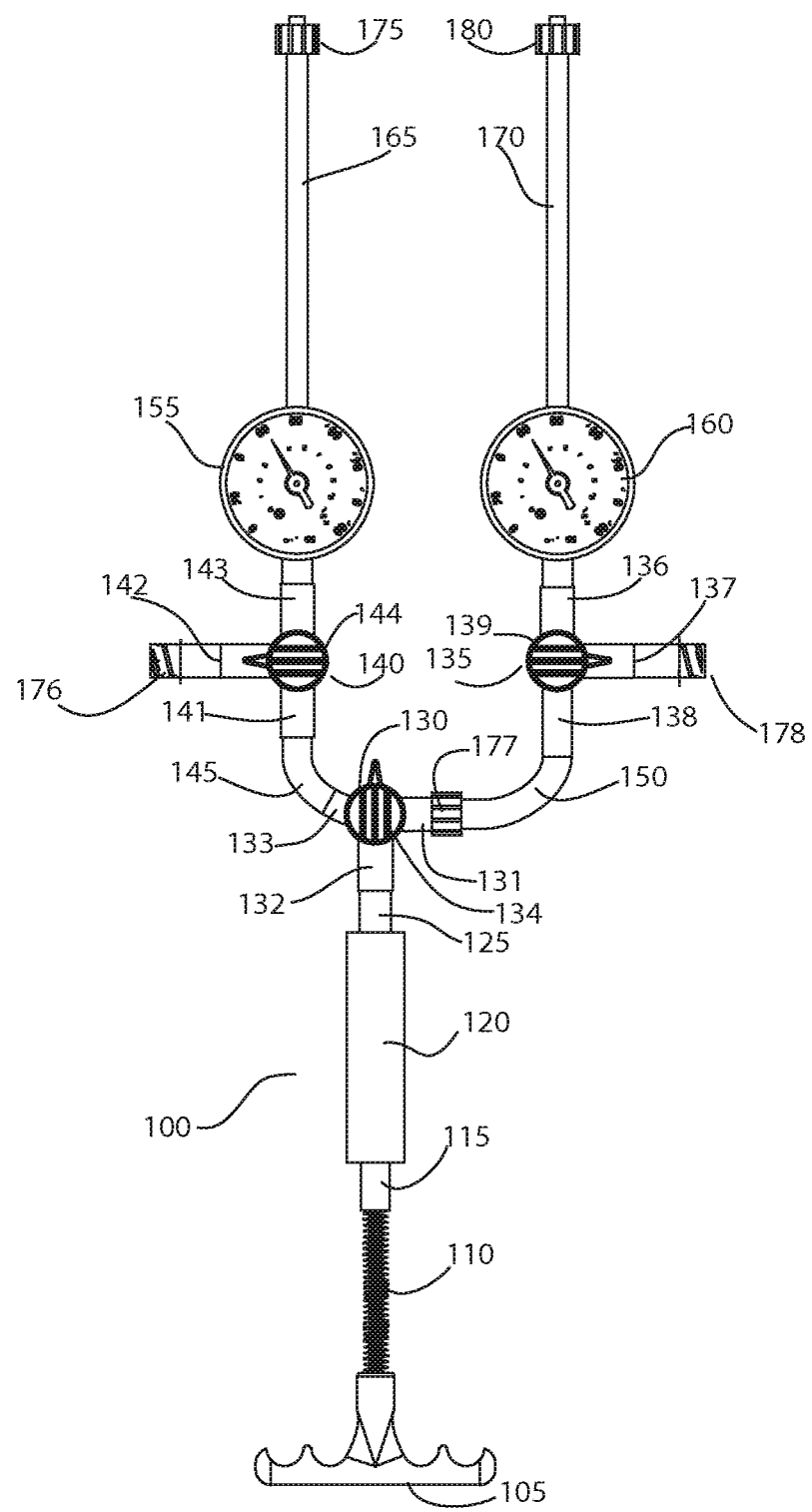
FIG. 1 provides a plan view of exemplary flow control components for an exemplary fluid dispensing and monitoring device for balloon angioplasty with two balloon catheters according to principles of the invention.
Figure 2:
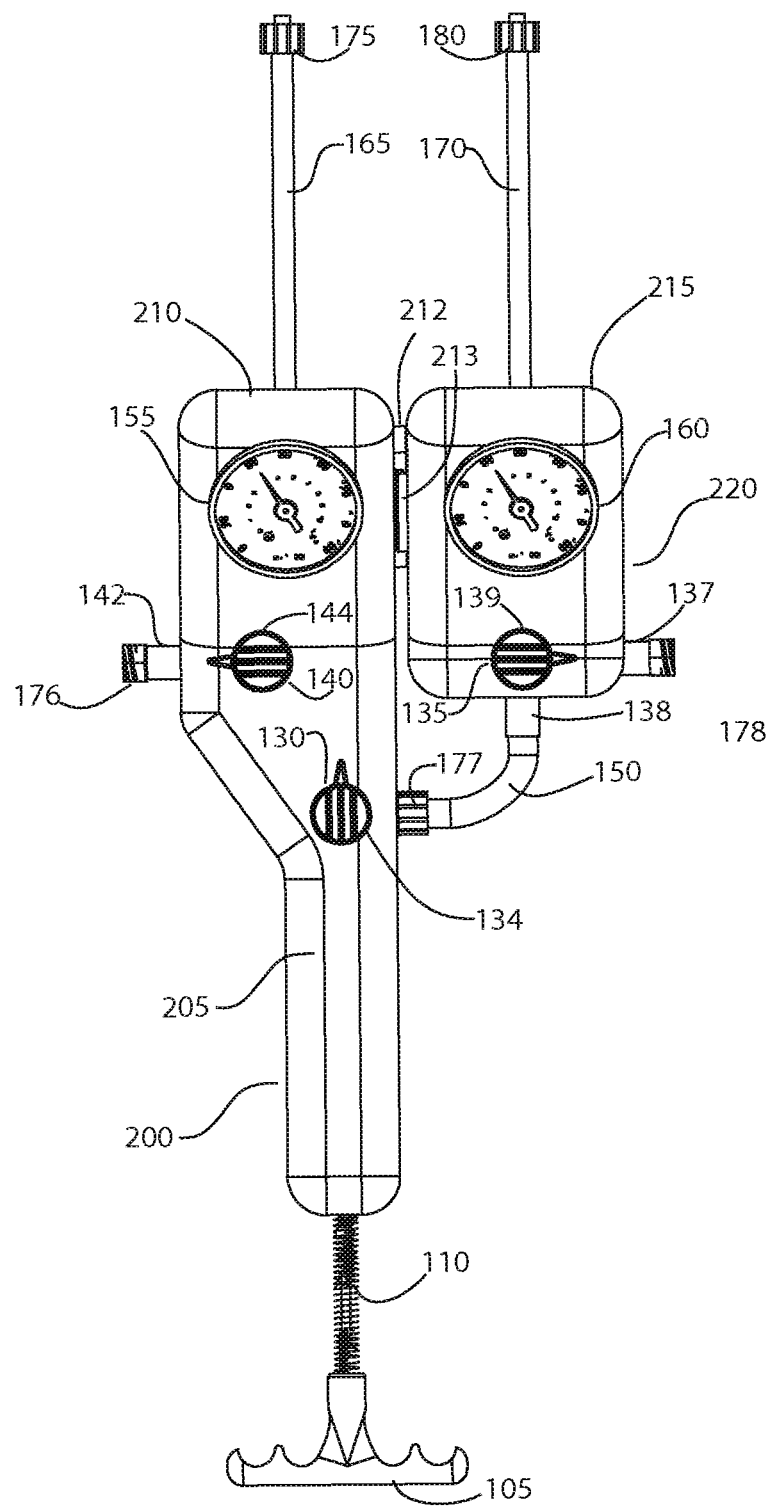
FIG. 2 provides a plan view of primary and secondary modules for an exemplary fluid dispensing and monitoring device for balloon angioplasty with two balloon catheters according to principles of the invention.
Figure 3:
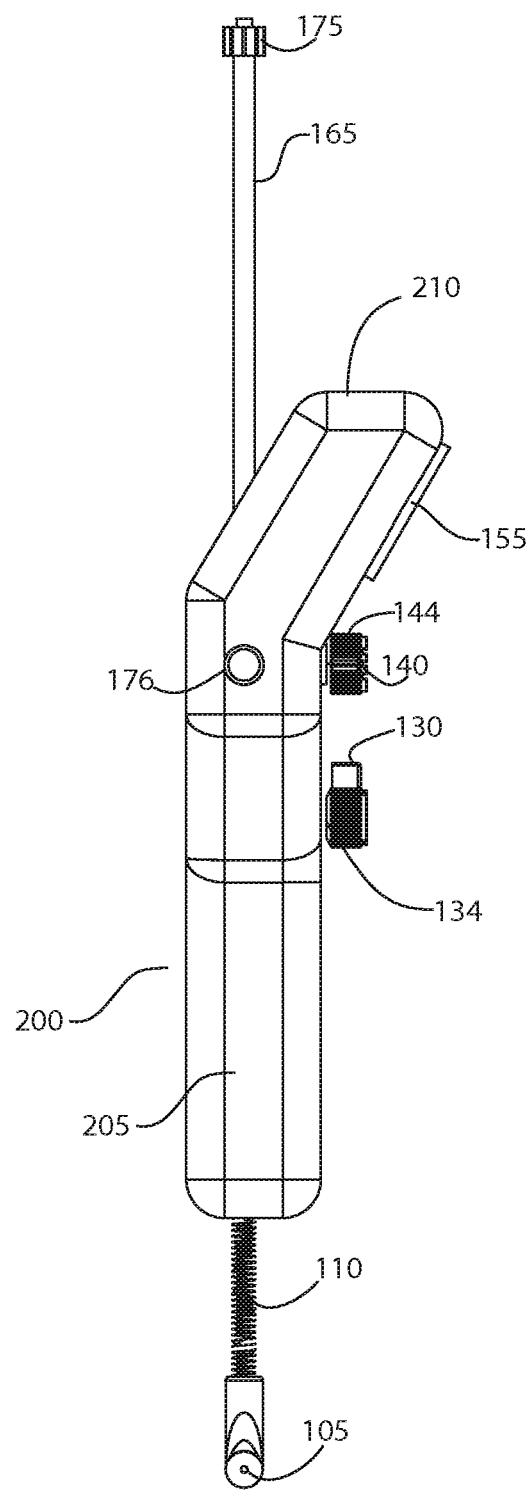
FIG. 3 provides a side view of an exemplary dispensing and monitoring device for balloon angioplasty with two balloon catheters according to principles of the invention.
Figure 4:
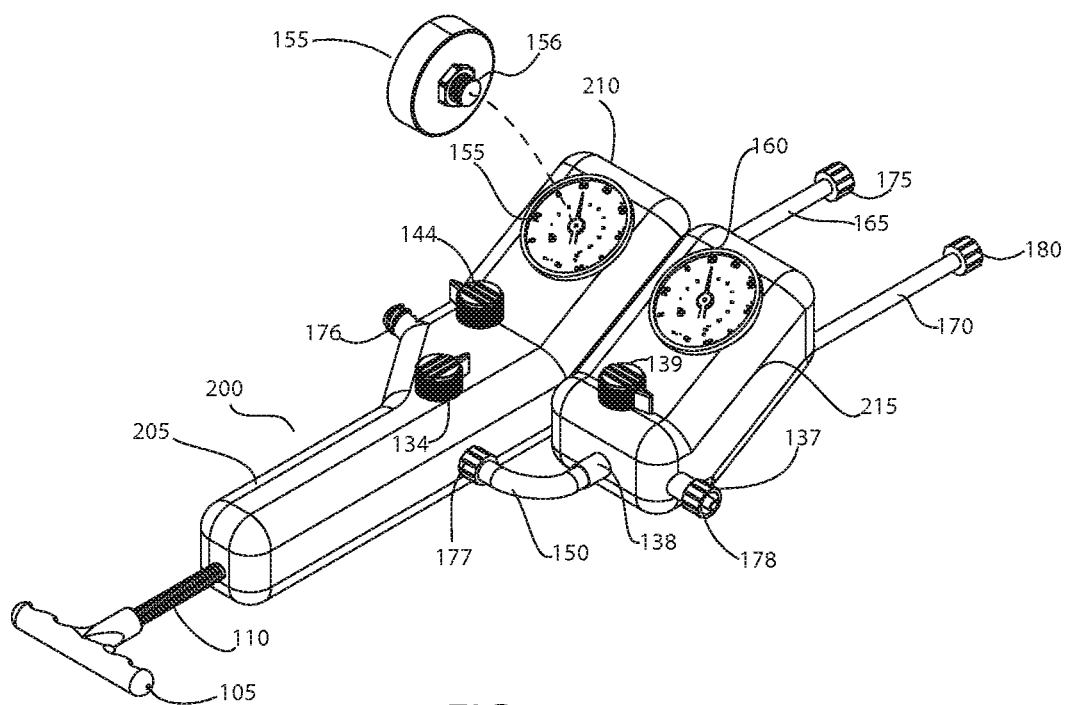
FIG. 4 provides a perspective view of an exemplary dispensing and monitoring device for balloon angioplasty with two balloon catheters according to principles of the invention.
Figure 5:
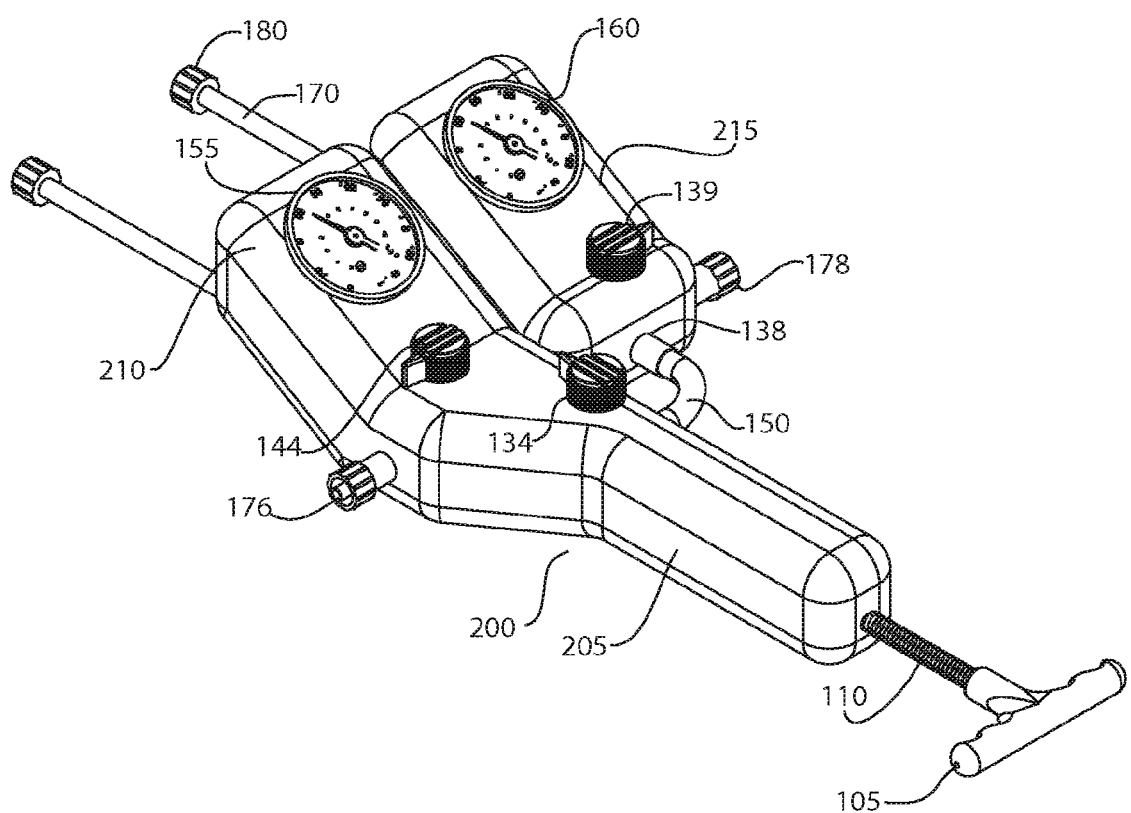
FIG. 5 provides a first perspective view of an exemplary dispensing and monitoring device for balloon angioplasty with two balloon catheters according to principles of the invention.
Figure 6:
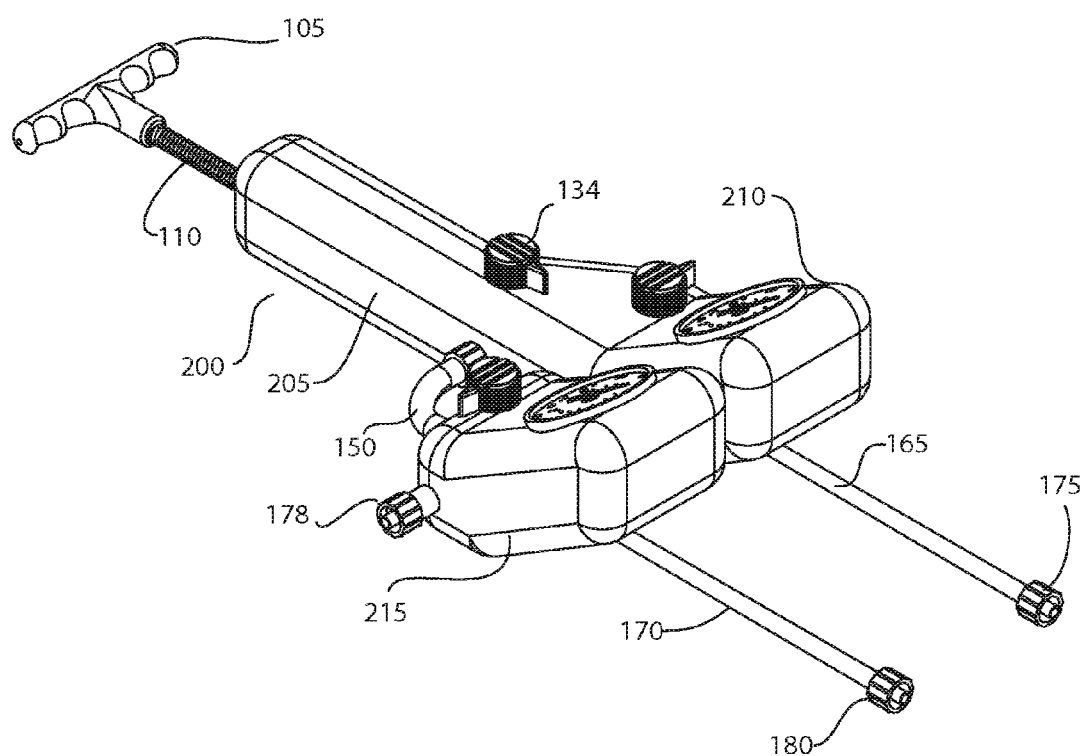
FIG. 6 provides a second perspective view of an exemplary dispensing and monitoring device for balloon angioplasty with two balloon catheters according to principles of the invention.

Referring to FIG. 1, an exemplary flow control assembly 100 for an exemplary fluid dispensing and monitoring device (i.e., inflator/deflator or "indeflator") for balloon angioplasty with two balloon catheters according to principles of the invention is conceptually illustrated. The assembly includes a pumping mechanism, i.e., fluid dispensing and aspirating mechanism, such as a syringe-like mechanism comprised of a tubular body 120 with an outlet 125, a threaded collar 115 receiving a threaded shaft 110 with a handle 105. The pumping mechanism is described in greater detail below.

An indeflator, according to principles of the invention, includes a manifold attached to the outlet of the pump. An exemplary manifold is comprised of a three-port valve 130 and a plurality of tubes 145, 131. The manifold can be fluidly coupled to two separate fluid channels 165, 170. An angioplasty catheter is attachable to the outlet ports 175, 180 of each of the two separate fluid channels 165, 170. Thus, the manifold has a port 132 coupled to the outlet 125 of the pump, and two ports 136, 143 coupled to the fluid channels 165, 170.

Three separate three-port valves 130, 135, 140, control fluid communication between the pump and manifold and between the manifold and each fluid channel 165, 170. A primary three port valve 130 has one port 132 coupled to the outlet 125 of the pump and one port 133 coupled to one branch (e.g., tube) 145 of the manifold and another port 131 coupled to another branch 150 of the manifold via a releasable coupling 177. Each branch 145, 150 of the manifold comprises a fluid transmitting channel or tube. A first branch three port valve 140 includes one port 141 coupled to the outlet of a first branch 145 of the manifold, another port 143 coupled to a first fluid channel 165 and a third port 142 is free (i.e., an accessory port available for fluidly coupling an attachment). A second branch three port valve 135 includes one port 138 coupled to the outlet of the second branch 150 of the manifold, another port 136 coupled to a second fluid channel 170 and a third port 137 is free (i.e., an accessory port available for fluidly coupling an attachment). The free ports are accessory ports, each of which includes a releasable coupling 176, 178, e.g., a Luer-Lock fitting, for accessory attachment. The secondary module 215 described below is releasably attachable to the primary module 210, also described below, via releasable coupling 177.

Male and female couplings are interchangeable. By way of example, on component may have a male coupling while a mating component has a female coupling, or vice versa. Thus, the invention is not limited to any particular arrangement of male and female couplings, so long as the couplings mate together to form a fluid path as described herein.

The primary valve 130 has four settings. In a first setting, all ports 131, 132, 133 of the valve 130 are in fluid communication. This setting allows flow between the pump and each branch 145, 150. In a second setting, port 131 and 132 are in fluid communication. This setting allows flow between the pump and one branch 150. In a third setting, port 132 and 133 are in fluid communication. This setting allows flow between the pump and the other branch 145. In a fourth setting, ports 131 and 133 are in fluid communication. This setting prevents flow between the branches 145, 150 and the pump, while allowing flow between the branches 145, 150. The various settings are attained by rotating the control knob 134 and attached valve stem to a position corresponding to the desired setting.

The first branch three port valve 140 has four settings. In a first setting, all ports 141, 142, 143 of the valve 140 are in fluid communication. This setting allows flow between the accessory port 142 and each other port 141, 143. In a second setting, port 141 and 142 are in fluid communication. This setting allows flow between the accessory port 142 and one branch 145. In a third setting, port 142 and 143 are in fluid communication. This setting allows flow between the accessory port 142 and the channel 165. In a fourth setting, ports 141 and 143 are in fluid communication. This setting prevents fluid communication with the accessory port 142, while allowing flow between the branch 145 and channel 165. The various settings are attained by rotating the control knob 144 and attached valve stem to a position corresponding to the desired setting.

Likewise, the second branch three port valve 135 has four settings. In a first setting, all ports 136, 137, 138 of the valve 135 are in fluid communication. This setting allows flow between the accessory port 137 and each other port 136, 138. In a second setting, port 138 and 137 are in fluid communication. This setting allows flow between the accessory port 137 and one branch 150. In a third setting, port 136 and 137 are in fluid communication. This setting allows flow between the accessory port 137 and the channel 170. In a fourth setting, ports 136 and 138 are in fluid communication. This setting prevents fluid communication with the accessory port 137, while allowing flow between the branch 150 and channel 170. The various settings are attained by rotating the control knob 139 and attached valve stem to a position corresponding to the desired setting. In the preferred embodiment, the second branch 3-port valve 135 and its associated plumbing is selectively attachable to the primary valve 130, when needed for a second balloon catheter. Thus the first branch 3-port valve 140 may be used with or without the second branch 3-port valve 135.

Accessory ports 137, 142, 177, 182 and outlet ports 175, 180, are ports to which lines or equipment may attach. Such ports 137, 142, 175, 180 allow the controlled evacuation of catheters, introduction of contrast media, saline, and wire guides as well as waste removal and attachment of catheters. Any port configuration suitable for mating with corresponding lines and equipment may be utilized. By way of example and not limitation, some or all available ports may have a Luer-Slip fitting that conform to Luer taper dimensions and are pressed together and held by friction.

Before using a balloon catheter, the catheter is substantially evacuated. The accessory ports 137, 142 may be used to evacuate air from attached balloon catheters. An evacuated syringe may be attached to each accessory port 137, 142, via releasable couplings 176, 178, with each intermediate valve 135, 140 set to allow fluid communication between the accessory port 137, 142 and the channel port 136, 143 coupled to each channel 165, 170. By aspiration through the syringe, a negative pressure may be applied to each accessory port 137, 142. Air from each attached balloon catheter is drawn through the channel 165, 170, into the syringe through the accessory port 137, 142. The intermediate valves 135, 140 may then be set to prevent fluid flow between the accessory port 137, 142 and the channel port 136, 143. These steps may be repeated if further aspiration is necessary to sufficiently evacuate the balloon catheter before inflation fluid is introduced. Other evacuation techniques may be implemented through the accessory ports 137, 142 and intermediate valves 135, 140. Thus, the invention facilitates evacuation of attached balloon catheters and maintains the evacuated balloon catheters in a substantially evacuated state until an inflating fluid will be introduced.

Figures 19, 20:
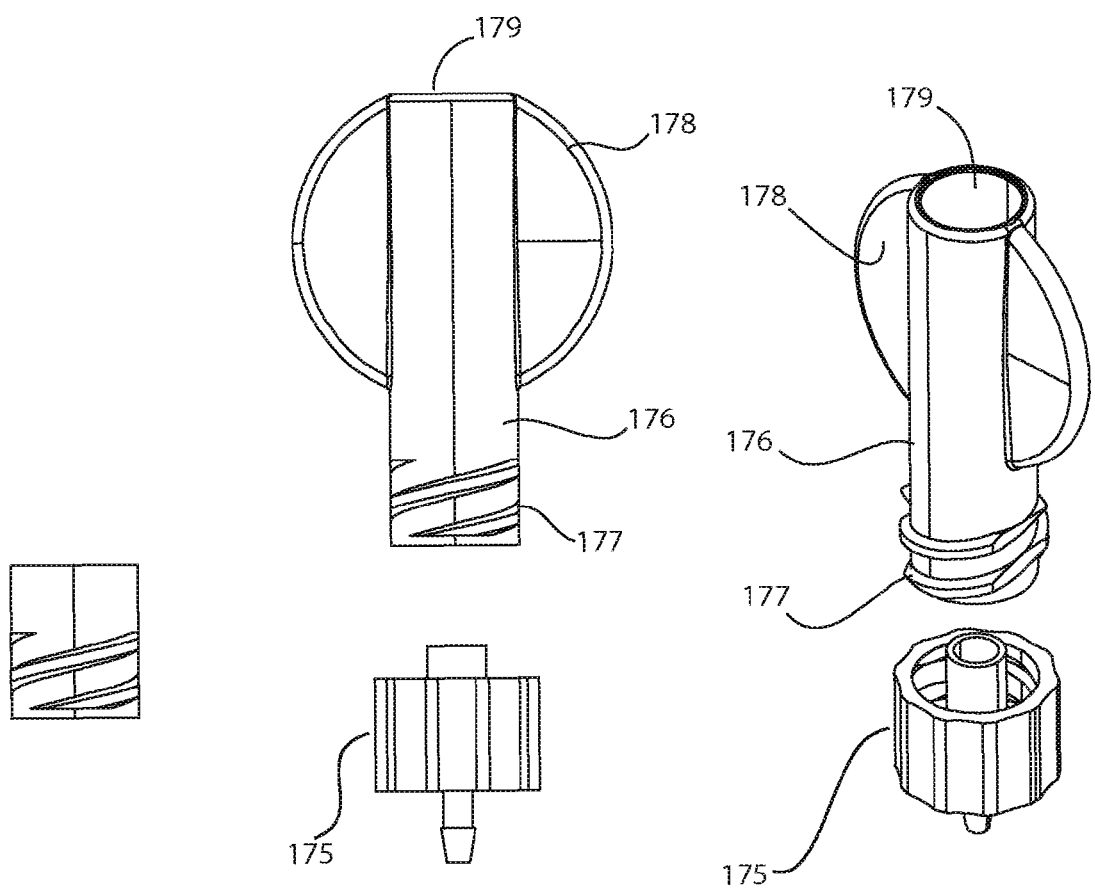
FIG. 19 provides a plan view of of an exemplary Luer-Lock fitting for an exemplary dispensing and monitoring device for balloon angioplasty with two balloon catheters according to principles of the invention.
FIG. 20 provides a perspective view of an exemplary Luer-Lock fitting for an exemplary dispensing and monitoring device for balloon angioplasty with two balloon catheters according to principles of the invention.
Figure 21:
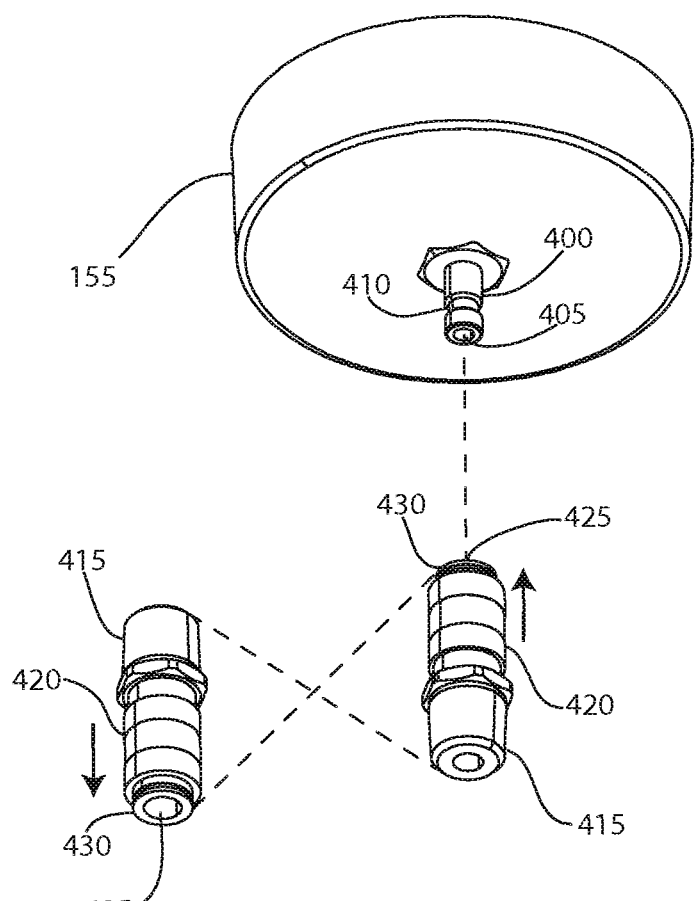
FIG. 21 conceptually illustrates a pressure gauge with a quick disconnect coupling for releasable attachment to a dispensing and monitoring device for balloon angioplasty according to principles of the invention.

In an exemplary implementation, outlet ports 175, 180 are Luer-Lock fittings, suitable for attachment to a balloon catheter for angioplasty. Releasable couplings 176, 178 are also Luer-Lock fittings. As conceptually illustrated in FIGS. 19 and 20, an exemplary Luer-Lock fitting may be securely joined by means of a tabbed 178 threaded 177 hub 176 on a female fitting (e.g., the fitting on the end of the line or equipment to be attached, such as the catheter) with an outlet 179 coupled to the attached line or equipment. The female fitting screws into threads in a sleeve 175 on a male fitting (e.g., the port). The sleeve 175 may be rotatable relative to a tube to which it is coupled. Rotation of the sleeve 175 allows connection to a threaded mating member 177, without twisting and kinking of tubing.

A pressure measuring instrument 155, 160, such as a manometer, aneroid gauge, bourdon gauge, or an electronic pressure sensor (each a "pressure gauge"), is fluidly coupled to each fluid channel 165, 170. The pressure measuring instrument senses and displays fluid pressure in the coupled fluid channel over a useful range of pressures, such as from about 0 to 30 atmospheres. This range encompasses the pressures applied to inflate balloons in most angioplasty procedures. Another scale, e.g., psi, may also be displayed on the face of the primary measuring instrument. In the exemplary embodiment, the device includes two separate channels 165, 170, one for each balloon catheter. Therefore, in the exemplary embodiment, there are two separate pressure measuring instruments 155, 160, one pressure measuring instrument for each channel. The three port valves 130, 135, 140 allow each channel 165, 170 to be isolated from each other and also allow each channel 165, 170 to be independently coupled to the pump. Consequently, pressure may be monitored independently in each channel 165, 170. Additionally, a different pressure may be applied in each channel 165, 170. Furthermore, pressure may be equilibrated between the channels 165, 170.

With reference to FIGS. 2 through 6, an exemplary inflating, deflating, dispensing and monitoring device 200 for balloon angioplasty is conceptually illustrated. The device is shown with a primary indeflator module 205 and an attached secondary module 215. The primary module 205 contains fluid management components for inflation, deflation, dispensing and monitoring, for balloon angioplasty through a catheter attached to fluid channel 165 via Luer-Lock sleeve 175. The secondary module 215 contains fluid management components for inflation, deflation, dispensing and monitoring, for balloon angioplasty through a catheter attached to fluid channel 170 via Luer-Lock sleeve 180. The assembled device includes all of the components of the assembly 100 of FIG. 1. A housing 200 with a handle 205 and two prongs 210, 215 contains portions of the assembly. Valves control knobs 134, 139, 142 extend through the housing 200. Pressure gauges 155, 160 either extend through the housing 200 or are readable through transparent lenses in the housing. The threaded shaft 110 and knob-like handle 105 of the syringe-like pump assembly extend from the handle 205 of the housing 200. Channels 165, 170 and channel valves 175, 180 extend from the prongs 210, 215 of the housing 200.

The secondary module 215 may be attached to the primary module 205, if and when needed for treatment of a bifurcated lesion. Thus, illustratively, radiometry of an obstructed artery containing an angioplasty catheter with a lumen containing radiopaque fluid may reveal a bifurcation lesion in a clinically relevant side branch. In such a case, the secondary module 215 may be attached to treat the main branch and side branch as part of the same procedure. Advantageously, the secondary module 215 may be attached without removal of the deployed primary catheter. If a procedure does not reveal a bifurcation legion in a clinically relevant side branch, then the primary module 205 may be used without the secondary module 215. In this manner, time and cost are saved. The supplemental module 215 is used only when needed and may be rapidly attached using Luer-Lock sleeve 177 or a similar fluid coupling, without disrupting a procedure in progress.

To avoid confusion between the separate channels 165, 170, the prongs 210, 215 gauges 155, 160, and intermediate valves 137, 142, may be color coded. For example, the components associated with one side may have a first color, while the components of the other side may have a second color. Illustratively, one color may be blue or some other color, and the other may be red or some other readily distinguishable color. A practitioner will choose and know which color corresponds to a branch and which color corresponds to a main vessel during use. To further avoid confusion, the surface of the prongs 210, 215 may be markable with a marker. Thus, a practitioner may write a distinguishing notation on each prong 210, 215, such as B for branch and M for main. In yet another embodiment, such distinctive lettering may be provided on the prongs 210, 215, such as by embossing, printing, decals or other means of applying characters to a surface.

Now referring to FIGS. 3 through 6 and 8, the portion of the housing containing the pressure gauge 155, 160 in each of the primary 210 and secondary modules 215 is bent or angled, placing the gauges in the user's line of sight.

As best seen in FIGS. 7 through 12, mating male and female clips 212, 213 allow mechanical attachment of the secondary module 215 to the primary module 210. A hook-like male clip 213 of the secondary module 215 slides into and is received and held by a female receptacle 212. The hook-like male clip 213 may comprise a snap-fit connection with elements that deflect for engagement and return to their undeflected position after engagement to resist unintended withdrawal.

Figure 7:
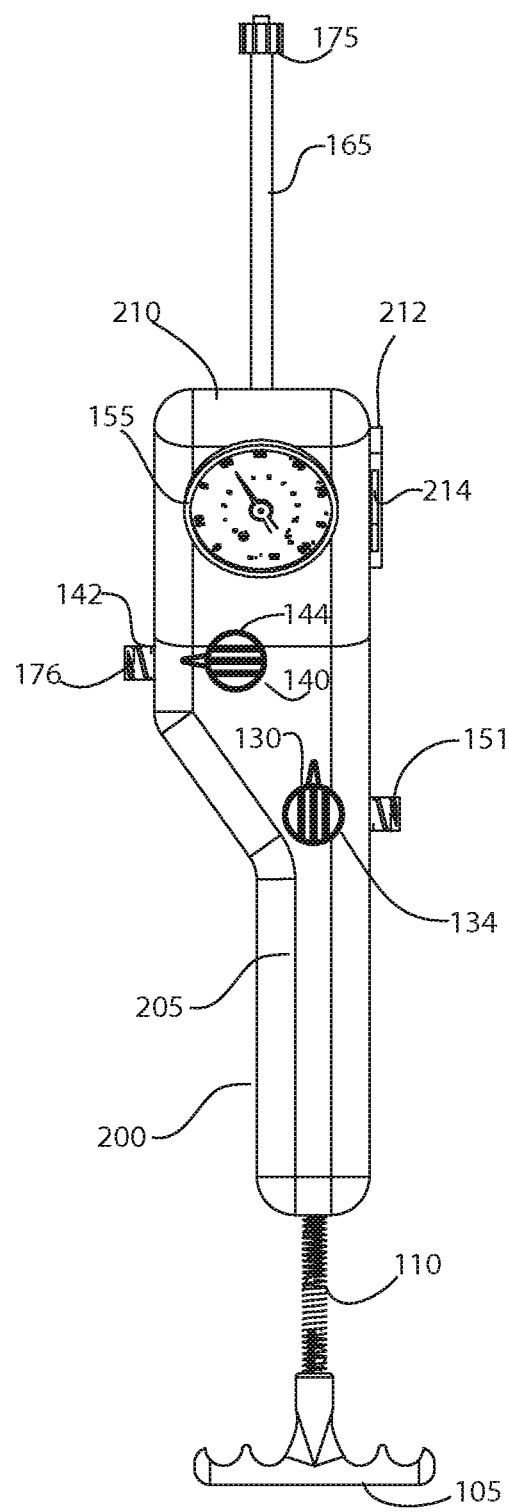
FIG. 7 provides a plan view of a primary module portion for an exemplary dispensing and monitoring device for balloon angioplasty with two balloon catheters according to principles of the invention.
Figure 8:
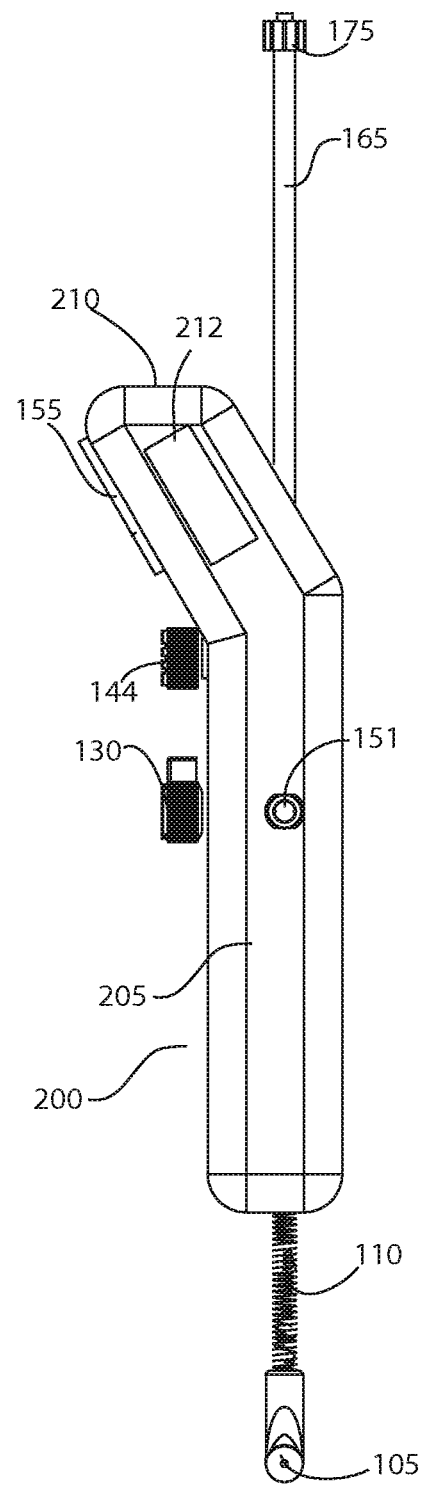
FIG. 8 provides a side view of a primary module portion for an exemplary dispensing and monitoring device for balloon angioplasty with two balloon catheters according to principles of the invention.
Figure 9:
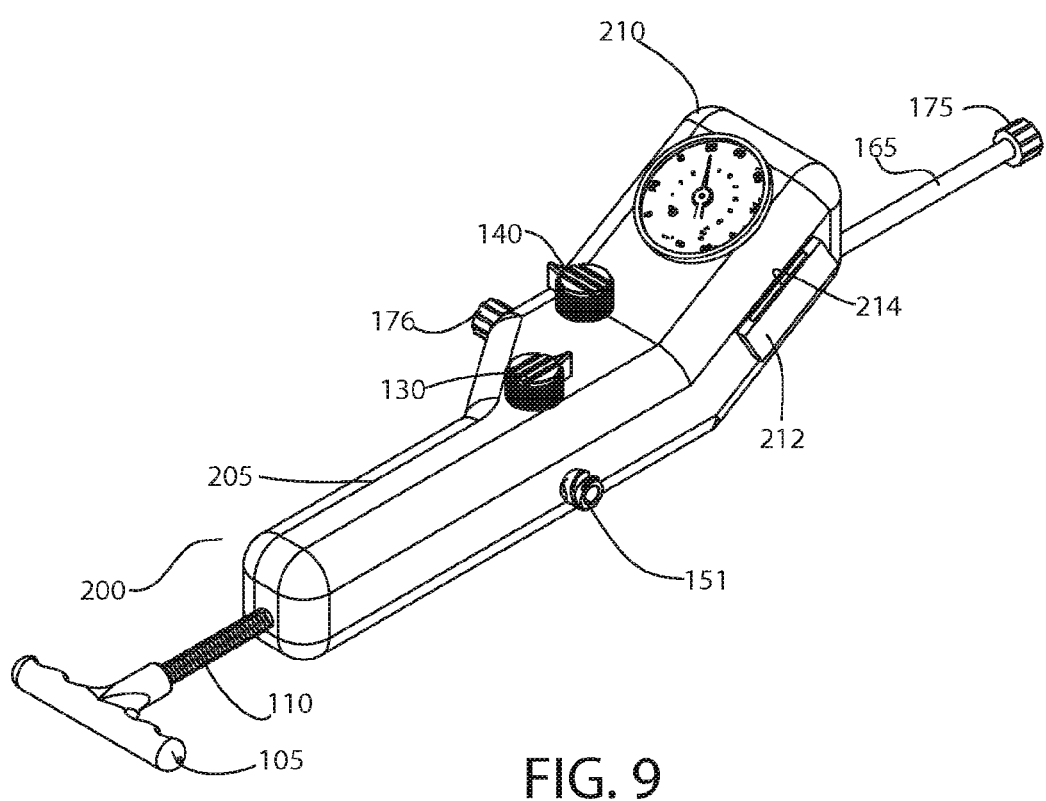
FIG. 9 provides a perspective view of a primary module portion for an exemplary dispensing and monitoring device for balloon angioplasty with two balloon catheters according to principles of the invention.
Figure 10:
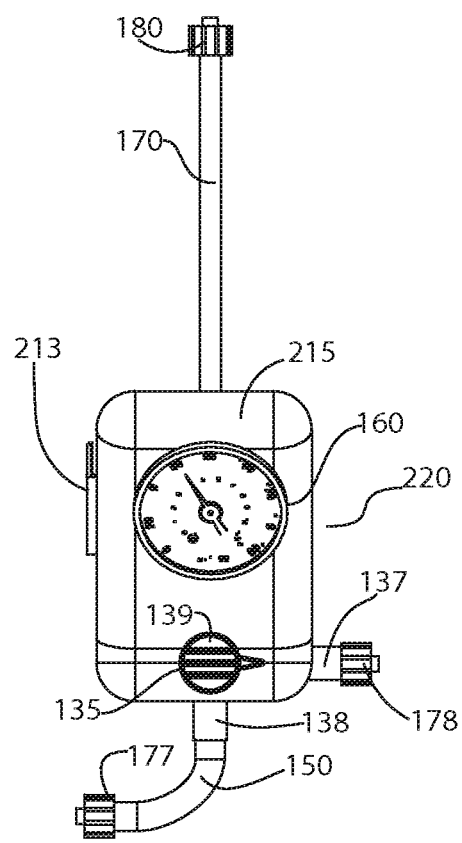
FIG. 10 provides a plan view of a secondary module portion for an exemplary dispensing and monitoring device for balloon angioplasty with two balloon catheters according to principles of the invention.
Figure 11:
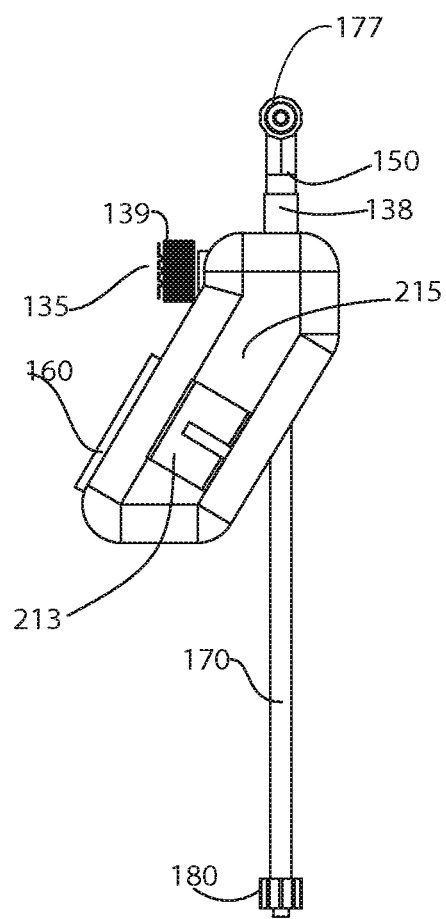
FIG. 11 provides a side view of a secondary module portion for an exemplary dispensing and monitoring device for balloon angioplasty with two balloon catheters according to principles of the invention.
Figure 12:
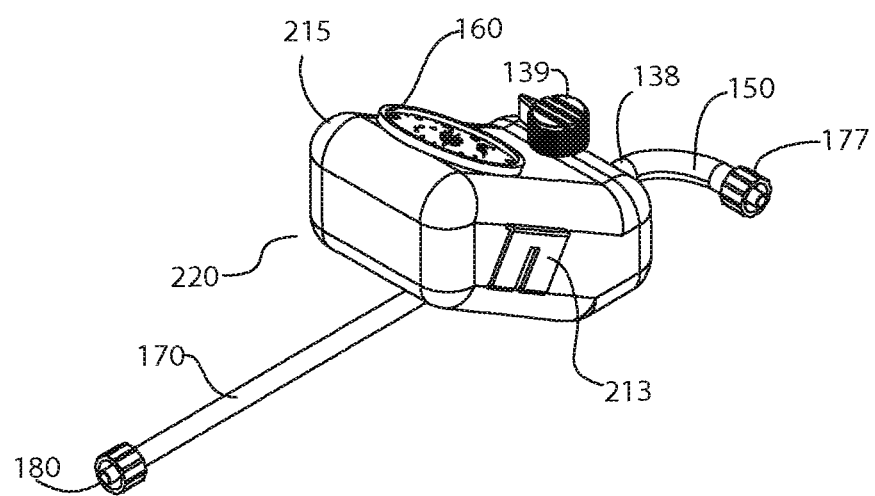
FIG. 12 provides a perspective view of a secondary module portion for an exemplary dispensing and monitoring device for balloon angioplasty with two balloon catheters according to principles of the invention.

FIGS. 7 through 9 illustrate an exemplary primary module 210, as described above, without the attachable secondary module 215. FIGS. 10 through 12 illustrate an exemplary secondary module 215, as also described above, apart from the primary module 210.

In one embodiment, the pressure gauges 155, 160 are permanently attached. In another embodiment, illustrated in FIG. 4, the pressure gauges 155, 160 may be removably attached. By way of example and not limitation, each pressure gauges may include a threaded male plug 156 that mates with a female threaded outlet in fluid communication with the corresponding channel 165, 170. In this embodiment, the gauges may be replaced for a particular procedure. Thus, a gauge configured for readings between 1 and 30 atm may be replaced with a gauge configured for readings between 1 and 20 atm, with higher resolution. Similarly, a gauge configured for readings between 1 and 20 atm may be replaced with a gauge configured for readings between 1 and 30 atm, to facilitate a procedure that may require high pressure. Concomitantly, the gauges 155, 160 may be the same or different. In the latter case, one gauge (e.g., a main vessel gauge) may be configured for higher readings than a side branch vessel gauge, or vice versa. In this manner, pressure gauges of an indeflator according to principles of the invention may be selected and installed for a particular procedure.

As an alternative to the threaded fitting as described above, a quick connect coupling may be used to provide a fast, make-or-break connection between each pressure gauge 155, 160 and each corresponding fluid channel 165, 170. In one embodiment, as conceptually illustrated in FIG. 31, a quick connect coupling comprised of a female fitting 415 and a mating male fitting 400 may be provided. The female fitting 415 would replace the female threaded outlet 157, 162, described above, in fluid communication with the corresponding channel 165, 170. The male fitting 400, which is comprised of a tube 405 with a recessed collar 410, extends from the pressure gauge 155 to provide fluid communication to the pressure gauge 155 through the tube 405. The tube 405 is shaped and sized to mate with the female fitting 415 in fluid communication with channels 165, 170. The female fitting 415 has an elastomeric diaphragm that provides a leak-proof seal until the diaphragm is pushed open by the end of the tube 405 of the male fitting 400. A movable outer collar 420 is biased in a position on the female fitting 415 by a spring. When the tube 405 of the male fitting 400 is inserted into the mating channel 425 of the female fitting 415, a ring of ball bearings held beneath the movable outer collar 420 engages the recessed collar 410 of the male fitting 400 and holds the male fitting 400 in place. To release the male fitting 400, the collar 420 is moved in a direction opposed to the spring bias, e.g., forward (towards the free end 430 of the female fitting), thereby releasing the ring of ball bearings from the recessed collar 410. When the male fitting 400 is removed, the diaphragm closes and prevents fluid from escaping from the female fitting 415. In this embodiment, sufficient space is provided between the bottom of each pressure gauge 155 and the corresponding surface of the prong 230 of the indeflator device to allow a user to grip and manipulate the movable collar 420 with the user's fingers.

Referring now to FIGS. 13 through 16, various views of an exemplary valve stem assembly for an exemplary dispensing and monitoring device for balloon angioplasty with two balloon catheters according to principles of the invention is conceptually illustrated. An exemplary three port valve comprises a rotatable valve stem 300 with a T-shaped fluid passage comprised of converging channels 310, 315, 320 extending through the stem in a T-shaped configuration. Openings of the T-shaped fluid passage defined by the channels 310, 315, 320 may be rotated into alignment with the three ports of each three port valve, such as ports 132, 133, 134 for valve 130. As the valve stem 300 is rotated, the openings move into and out of alignment with a port, thereby opening or sealing the port.

A toroidal O-ring 305 sits in a depression on the stem and a corresponding depression in the tubular housing of the valve to provide a fluid-tight seal. A three port valve according to principles of the invention allows all three ports to be opened and in fluid communication and two ports to be open and in fluid communication. In embodiments where the channels 310, 315, 320 are sized and positioned such that a turn of the valve stem that is less than 90° (e.g., a 45° turn) places all channels 310, 315, 320 out of alignment with the ports, then all ports may be blocked. The invention is not limited to a particular three port valve. Valves and valve assemblies other than the exemplary manual three port valve described herein may be utilized without departing from the scope of the invention.

In an alternative implementation, certain three-port valves may have a rotatable valve stem with an L-shaped fluid passage extending through the stem, instead of the T-shaped passage shown in FIG. 15. In this embodiment, only two orthogonal ports can be in fluid communication with the L-shaped fluid passage at a time.

The invention includes a manually actuated syringe-like pump to inject fluid. The invention is not limited to a particular pump. Rather any pump suitable for dispensing fluid in a controlled manner for use in an indeflator for inflating a balloon of a balloon catheter for angioplasty may be utilized, with the caveat that the plump have a volumetric pumping capacity to provide sufficient fluid to inflate two separate balloon catheters and further that the pump support the required range of pressures for inflation.

Figure 17:
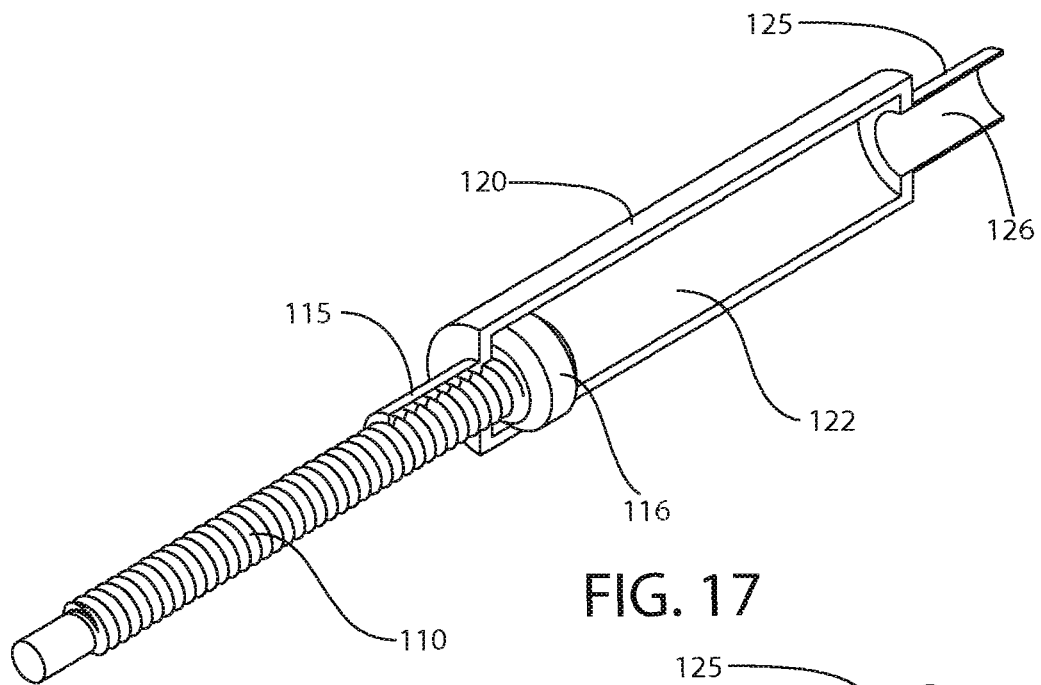
FIG. 17 provides a perspective view of a cutaway portion of an exemplary plunger in a first state for balloon angioplasty with two balloon catheters according to principles of the invention.
Figure 18:
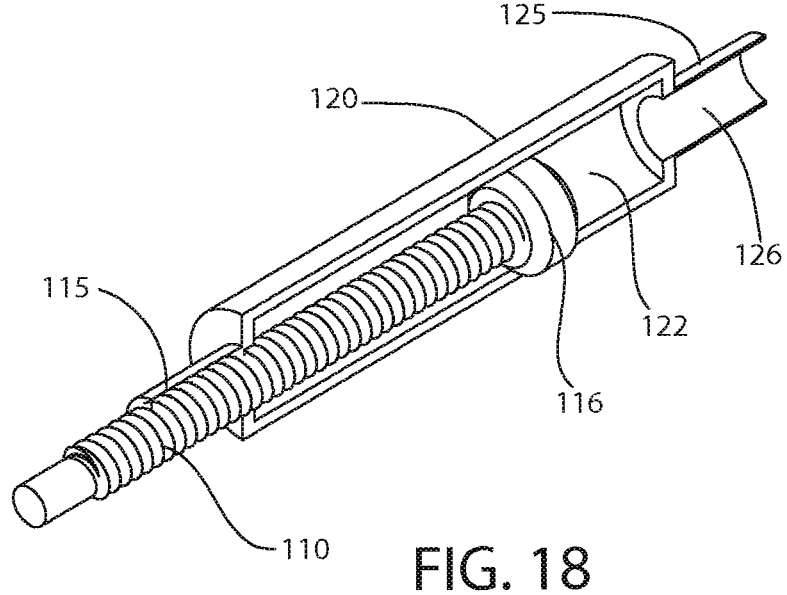
FIG. 18 provides a perspective view of a cutaway portion of an exemplary plunger in a second state for balloon angioplasty with two balloon catheters according to principles of the invention.

With reference to FIGS. 17 and 18, an exemplary pump comprises a tubular body 120 with an outlet 125 at the distal end. The body 120 defines a chamber 122. The outlet 125 defines an outlet channel 126. A piston 116 disposed in the chamber 122 of the tubular body 120 is movable linearly within the chamber 122 along the longitudinal axis of the body 120. The periphery of the piston 116 provides a fluid seal against the interior surface of the tubular body 120. A shaft, such as threaded shaft 110, extends from the piston 116. The threaded shaft 110 is threadedly received by a threaded bushing 115 at the proximal end of the tubular body 120 opposite the outlet 125. An actuator knob or ergonomic handle 105 (FIGS. 1-4) is attached to the end of the threaded shaft 110 that is opposite the piston 116. Rotation of the knob 105 in one direction, causes the threaded shaft 110 to rotate in the same direction and advances the piston 116 in the tubular body towards the outlet 125. Rotation of the knob 105 in the other direction, causes the threaded shaft 110 to rotate and moves the piston in the tubular body away from the outlet 125. Advancement of the piston 116 towards the outlet 125 produces a positive pressure that expels fluid ahead of the piston 116 from the tubular body 120 through the outlet 125. Retreating motion of the piston 116 away from the outlet 125 produces a negative pressure differential that draws fluid into the tubular body 120 through the outlet 125. One or more releasable locks may be provided to releasably lock the shaft in a particular position.

To fill the pump with a fluid (e.g., saline), a saline source may be fluidly coupled to an accessory port, such as, but not limited to, port 142 of valve 140. The valve 140 with the accessory port may be configured to allow fluid communication between the accessory port 142 and the port 141 leading towards the pump. The primary valve 130 may be configured to allow flow between the port 133 nearest the accessory port 142 through which the fluid was introduced and the port 132 coupled to the outlet 125 of the pump. As the piston 116 is moved away from the outlet 125, fluid is drawn through the outlet channel 126 into the chamber 122 of the tubular body 120 between the piston 116 and the outlet channel 126. Similarly, fluid may be drawn into the pump via accessory ports 137, 177, 182 and via outlet ports 175, 180.

After being filled with a sufficient volume of fluid for inflating a pair of balloon catheters, the indeflator may be configured for inflation. For sequential inflation, fluid is forced through one channel 165 or 170 and out of the corresponding outlet port 175 or 180. For example, branch valve 140 may be configured to allow flow from port 141 to port 143. Primary valve 130 may be configured to allow flow from port 132 to port 133. Advancing the piston 116 towards the outlet 125 forces fluid from the pump through branch 145 and channel 165 and out of the outlet port 175, to which a balloon catheter may be connected. The pressure gauge 155 monitors pressure in the channel 165. When the desired pressure is reached, the channel 165 may be isolated. For example, valve 140 may be configured to prevent flow through port 143. Additionally, valve 130 may be configured to prevent flow through branch port 133. Elevated pressure in channel 165 will be maintained while the channel 165 is isolated. Furthermore, while pressure is maintained in channel 165, channel 170 may be pressurized to inflate a balloon catheter attached to outlet port 183. To do so, outlet valve 180 may be configured to allow flow from port 181 to port 183. Branch valve 135 may be configured to allow flow from port 138 to port 136. Primary valve 130 may be configured to allow flow from port 132 to port 131. Advancing the piston 116 towards the outlet 125 forces fluid from the pump through branch 150 and channel 170 and out of the outlet port 183, to which a balloon catheter may be connected. The pressure gauge 160 monitors pressure in the channel 170. When the desired pressure is reached, the channel 170 may be isolated. For example, valve 135 may be configured to prevent flow through port 136. Additionally, valve 130 may be configured to prevent flow through branch port 131. Elevated pressure in channel 170 will be maintained while the channel 170 is isolated.

Subsequently, the inflated balloon catheters may be deflated simultaneously or sequentially. In sequential deflation, the pressurized fluid may be exhausted from any accessory port in fluid communication with the corresponding channel. Alternatively, the pressurized fluid may be drawn back into the pump. Exhausting through an accessory port may entail configuring valve 140 to allow flow from port 143 to 142. If pressurized fluid will be drawn back into the pump, the valve configurations for inflation (as described above) are repeated and the piston 116 in the pump is moved away from the outlet 125, drawing fluid through the outlet channel 126 into the chamber 122 of the tubular body 120 between the piston 116 and the outlet channel 126. The deflated channel may then be isolated. The same deflation procedure may then be applied to the other channel 170.

For simultaneous kissing balloon inflation, valve 130 may be configured to allow flow through all ports 131, 132, 133. Valve 140 may be configured to allow flow from port 141 to port 143. Valve 135 may be configured to allow flow from port 138 to port 136. Then the pump forces fluid into each channel, inflating the balloon catheters. Advancing the piston 116 towards the outlet 125 forces fluid from the pump through branches 145, 150 and channels 165, 170 and out of the outlet ports 175, 180, to which balloon catheters may be connected. The pressure gauges 155, 160 monitor pressure in the channels 165, 170. When the desired pressure is reached, the channels 165, 170 may be isolated.

In this manner, each balloon catheter may be inflated and deflated, sequentially inflated, simultaneously inflated, sequentially deflated, simultaneously deflated, inflated to the same pressures, inflated to different pressures, partially deflated, and fully deflated. Pressure in each balloon catheter may be monitored. Through accessory ports 137, 142 fluids (e.g., saline or contrast media) may be introduced into or evacuated from a balloon catheter. Pressure gauges may be fixed and may be identical or different. Alternatively, pressure gauges may be removable and the same or different. Pressure gauges may be removed and replaced. Fluids (e.g., saline or contrast media) may be introduced or added to the pump and branches, even during a procedure, without deflating a catheter. An indeflator according to principles of the invention thus provides enhanced versatility over conventional indeflators, which do not facilitate simultaneous inflation or deflation, and do not allow removal of pressure gauges, and do not allow inflation and deflation of both balloon catheters through a single pump.

Now referring to FIG. 14, an exemplary ergonomic version of a dispensing and monitoring device for balloon angioplasty with two balloon catheters according to principles of the invention is conceptually illustrated. This embodiment includes a bend 220, 225 in each prong 210, 215, positioning the terminal portion 230, 235 of each prong 210, 215 in the line of sight of a user, while the user holds the handle 205. This configuration enhances visibility of the pressure gauges 155, 160 throughout an angioplasty procedure.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

The invention claimed is:

1. An expandable inflation device for up to two balloon catheters for angioplasty, said two balloon catheters including a first catheter and a second catheter, said inflation device comprising:

a pump mechanism having a tubular reservoir with an outlet and a longitudinal axis, and piston movable linearly through the tubular reservoir along the longitudinal axis, and a manually operated actuator coupled to said piston and controlling linear motion of the piston; and a primary three-port valve having a first primary port in fluid communication with the outlet of the pump, a second primary port and a third primary port, said primary three port valve being switchable between a first state in which the first primary port, second primary port and third primary port are in fluid communication, and a second state in which the first primary port and second primary port are in fluid communication, and a third state in which the first primary port and third primary port are in fluid communication, and a fourth state in which the second primary port and third primary port are in fluid communication; and a first pressure measuring device in fluid communication with the second primary port of the primary three-port valve; and a second pressure measuring device in fluid communication with and releasably attachable to the third primary port of the primary three-port valve; and a first outlet port in fluid communication with the first pressure measuring device and the second primary port of the primary three-port valve, said first outlet port being attachable to the first catheter; and a second outlet port in fluid communication with the second pressure measuring device and the third primary port of the primary three-port valve, said second outlet port being attachable to the second catheter.

2. The expandable inflation device for up to two balloon catheters for angioplasty according to claim 1, further comprising a left intermediate three-port valve disposed and fluidly coupled between said second primary port of the primary three-port valve and said first pressure measuring device, said left intermediate three-port valve having a first left intermediate port, a second left intermediate port and a third left intermediate port, and said left intermediate three port valve being switchable between a first state in which the first left intermediate port, second left intermediate port and third left intermediate port are in fluid communication, and a second state in which the first left intermediate port and second left intermediate port are in fluid communication, and a third state in which the first left intermediate port and third left intermediate port are in fluid communication, and a fourth state in which the second left intermediate port and third left intermediate port are in fluid communication, said first left intermediate port being fluidly coupled to the second primary port of the primary three-port valve, and said third third left intermediate port being fluidly coupled to the first pressure measuring device, and said second left intermediate port being available for accessory attachment.

3. The expandable inflation device for up to two balloon catheters for angioplasty according to claim 2, further comprising a right intermediate three-port valve disposed and fluidly coupled between said third primary port of the primary three-port valve and said second pressure measuring device, said right intermediate three-port valve having a first right intermediate port, a second right intermediate port and a third right intermediate port, and said right intermediate three port valve being switchable between a first state in which the first right intermediate port, second right intermediate port and third right intermediate port are in fluid communication, and a second state in which the first right intermediate port and second right intermediate port are in fluid communication, and a third state in which the first right intermediate port and third right intermediate port are in fluid communication, and a fourth state in which the second right intermediate port and third right intermediate port are in fluid communication, said first right intermediate port being fluidly coupled to the third primary port of the primary three-port valve, and said third third right intermediate port being fluidly coupled to the second pressure measuring device, and said second right intermediate port being available for accessory attachment.

4. The expandable inflation device for up to two balloon catheters for angioplasty according to claim 1, further comprising a right intermediate three-port valve disposed and fluidly coupled between said third primary port of the primary three-port valve and said second pressure measuring device, said right intermediate three-port valve having a first right intermediate port, a second right intermediate port and a third right intermediate port, and said right intermediate three port valve being switchable between a first state in which the first right intermediate port, second right intermediate port and third right intermediate port are in fluid communication, and a second state in which the first right intermediate port and second right intermediate port are in fluid communication, and a third state in which the first right intermediate port and third right intermediate port are in fluid communication, and a fourth state in which the second right intermediate port and third right intermediate port are in fluid communication, said first right intermediate port being fluidly coupled to the third primary port of the primary three-port valve, and said third third right intermediate port being fluidly coupled to the second pressure measuring device, and said second right intermediate port being available for accessory attachment.

5. The expandable inflation device for up to two balloon catheters for angioplasty according to claim 4, said second right intermediate port being fluidly coupled to a syringe.

6. The expandable inflation device for up to two balloon catheters for angioplasty according to claim 2, said second left intermediate port being fluidly coupled to a syringe.

7. The expandable inflation device for up to two balloon catheters for angioplasty according to claim 1, said first outlet port comprising a threaded fluid fitting.

8. The expandable inflation device for up to two balloon catheters for angioplasty according to claim 7, said second outlet port comprising a threaded fluid fitting.

9. The expandable inflation device for up to two balloon catheters for angioplasty according to claim 1, said second outlet port comprising a threaded fluid fitting.

10. The expandable inflation device for up to two balloon catheters for angioplasty according to claim 1, the first outlet port comprising a first Luer Lock fitting and the second outlet port comprising a second Luer Lock fitting.

11. The expandable inflation device for up to two balloon catheters for angioplasty according to claim 1, said manually operated actuator coupled to said piston of said pump mechanism comprising a threaded shaft having one end coupled to said piston and a proximal end opposite the end coupled to the piston.

12. The expandable inflation device for up to two balloon catheters for angioplasty according to claim 11, said manually operated actuator further comprising a graspable rotatable handle attached to the proximal end of the threaded shaft.

13. The expandable inflation device for up to two balloon catheters for angioplasty according to claim 1, said first pressure measuring device being threadedly engaged and removable.

14. The expandable inflation device for up to two balloon catheters for angioplasty according to claim 13, said second pressure measuring device being threadedly engaged and removable.

15. The expandable inflation device for up to two balloon catheters for angioplasty according to claim 1, said second pressure measuring device being threadedly engaged and removable.

16. The expandable inflation device for up to two balloon catheters for angioplasty according to claim 3, further comprising:
    a first fluid channel disposed between and in fluid communication with the first outlet port and the third left intermediate port,
    a first quick disconnect coupling fluidly coupling said first pressure measuring device to the first fluid channel.

17. The expandable inflation device for up to two balloon catheters for angioplasty according to claim 16, further comprising:

a second fluid channel disposed between and in fluid communication with the second outlet port and the third right intermediate port, a second quick disconnect coupling fluidly coupling said second pressure measuring device to the second fluid channel.

18. The expandable inflation device for up to two balloon catheters for angioplasty according to claim 3, said first outlet port, left intermediate three port valve, and first pressure measuring device being a first color, and said second outlet port, right intermediate three port valve, and second pressure measuring device being a second color.

19. The expandable inflation device for up to two balloon catheters for angioplasty according to claim 1, said primary three-port valve switched to allow simultaneous inflation and deflation of the first catheter and the second catheter through the first outlet port and the second outlet port respectively.

20. The expandable inflation device for up to two balloon catheters for angioplasty according to claim 1, said primary three-port valve switched to allow inflation and deflation of one of the first catheter through the first outlet port and the second catheter through the second outlet port, but to not allow inflation of the other of the first catheter through the first outlet port and the second catheter through the second outlet port.

* * * * *